US006899679B2

(12) United States Patent
Kawagishi et al.

(10) Patent No.: US 6,899,679 B2
(45) Date of Patent: May 31, 2005

(54) ULTRASONIC DIAGNOSIS APPARATUS AND ULTRASOUND IMAGING METHOD

(75) Inventors: Tetsuya Kawagishi, Kuroiso (JP); Yoshitaka Mine, Tochigi-Ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 09/912,632

(22) Filed: Jul. 26, 2001

(65) Prior Publication Data

US 2003/0060712 A1 Mar. 27, 2003

(30) Foreign Application Priority Data

Jul. 26, 2000 (JP) ..................................... P2000-225926

(51) Int. Cl.[7] .............................................. A61B 8/00
(52) U.S. Cl. ..................................................... 600/443
(58) Field of Search ................................. 600/437, 443, 600/447, 458, 444, 445, 467, 449, 455, 456, 457

(56) References Cited

U.S. PATENT DOCUMENTS

| | | | |
|---|---|---|---|
| 5,632,277 A | | 5/1997 | Chapman et al. |
| 5,891,038 A | | 4/1999 | Seyed-Bolorforosh et al. |
| 5,957,852 A | * | 9/1999 | Hossack et al. ............. 600/477 |
| 5,961,463 A | * | 10/1999 | Rhyne et al. ................ 600/458 |
| 5,980,459 A | * | 11/1999 | Chiao et al. ................. 600/447 |
| 6,063,033 A | * | 5/2000 | Haider et al. ............... 600/447 |
| 6,146,330 A | | 11/2000 | Tujino et al. |
| 6,155,981 A | * | 12/2000 | Ermert et al. ................ 600/453 |
| 6,186,950 B1 | * | 2/2001 | Averkiou et al. ............ 600/443 |
| 6,206,833 B1 | * | 3/2001 | Christopher ................. 600/443 |
| 6,210,332 B1 | * | 4/2001 | Chiao et al. ................. 128/916 |
| 6,213,946 B1 | * | 4/2001 | Brock-Fisher ............... 600/443 |
| 6,251,074 B1 | * | 6/2001 | Averkiou et al. ............ 600/447 |
| 6,306,095 B1 | * | 10/2001 | Holley et al. ................ 600/458 |
| 6,315,723 B1 | * | 11/2001 | Robinson et al. ............ 600/443 |
| 6,319,203 B1 | * | 11/2001 | Averkiou ..................... 600/443 |
| 6,358,210 B2 | * | 3/2002 | Gee et al. .................... 600/443 |
| 6,432,054 B1 | * | 8/2002 | Ustuner et al. .............. 600/437 |

* cited by examiner

*Primary Examiner*—Francis J. Jaworski
(74) *Attorney, Agent, or Firm*—Oblon, Spivak, McClelland, Maier & Neustadt, P.C.

(57) ABSTRACT

An ultrasonic diagnostic apparatus transmits ultrasonic pulses relevant to each scanning line twice, for example, while changing a center frequency of a bandwidth; acquires an electrical receiving signal that corresponds to an ultrasonic echo for such each transmission; applies filter processing with characteristics in accordance with a bandwidth of a harmonic component of a respective one of two receiving signals received for each scanning line; synthesizes the thus processed two receiving signals; and generates/displays an image by using the synthesized receiving signal. In this manner, the resolution and signal intensity in a depth direction is improved by broadening the bandwidth of a harmonic component provided for image generation, and a harmonic image having an occurrence of a motion artifact restrained is provided.

21 Claims, 10 Drawing Sheets

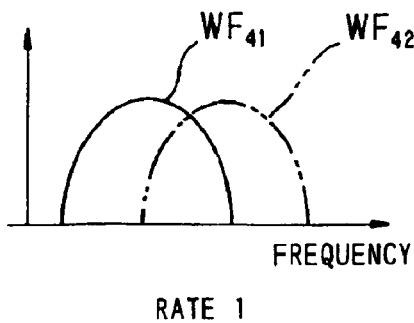
FIG. 3A  RATE 1
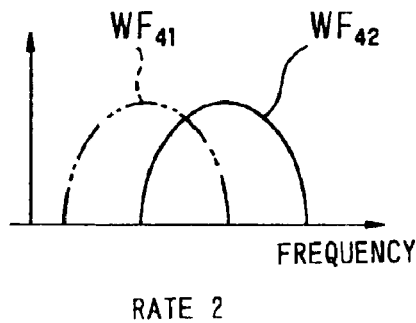
FIG. 3B  RATE 2
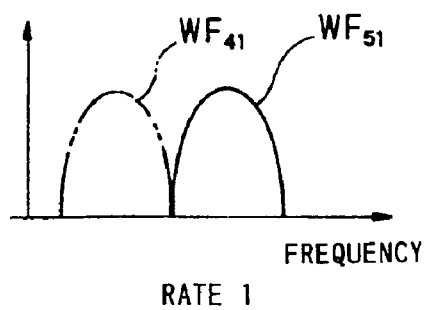
FIG. 4A  RATE 1
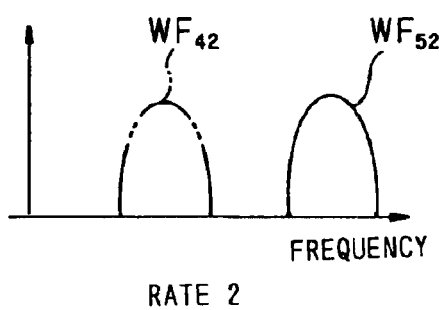
FIG. 4B  RATE 2
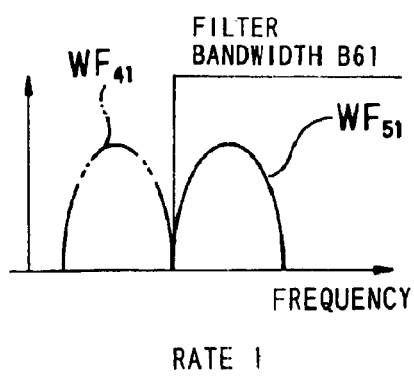
FIG. 5A  RATE 1
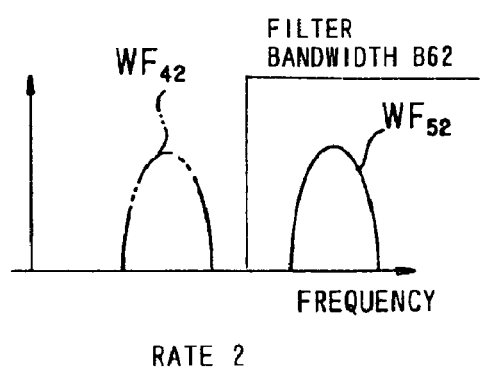
FIG. 5B  RATE 2

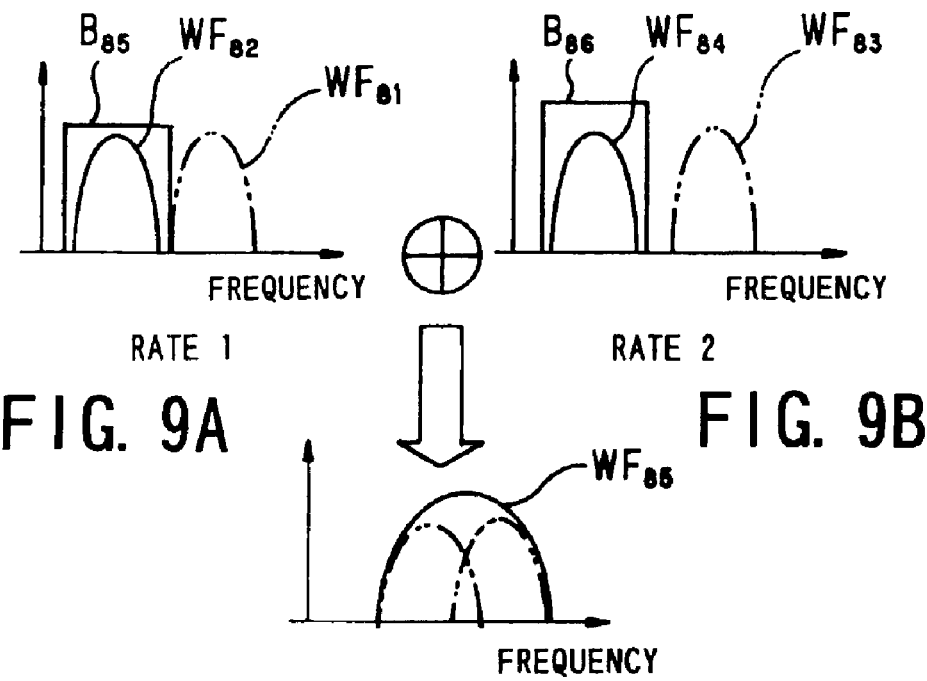
FIG. 9A  FIG. 9B
FIG. 9C
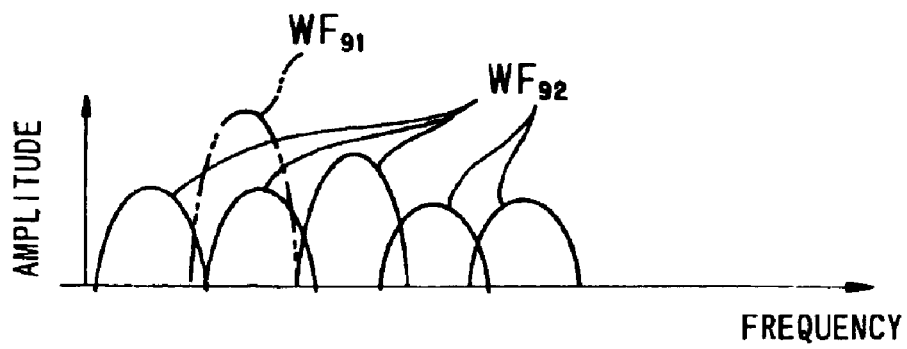
FIG. 10

(SUPERIMPOSITION OF FUNDAMENTAL
AND HARMONIC COMPONENTS)

ULTRASONIC DIAGNOSIS APPARATUS AND ULTRASOUND IMAGING METHOD

BACKGROUND OF THE INVENTION

1. Field of the Invention

The present invention pertains to a medical ultrasonic diagnostic apparatus and an ultrasonic imaging method. More particularly, the present invention relates to an ultrasonic diagnostic apparatus and an ultrasonic imaging method utilizing non-linearity when ultrasonic signals propagate tissues of a living body or non-linearity of a contrast medium when the contrast medium is administered to the living body, carrying out diagnosis, thereby sampling a non-linearity component of a transmission ultrasonic wave from a receiving signal and providing useful diagnostic information concerning tissue information or blood flow information.

2. Description of Related Art

In the field of the medical care, an ultrasonic diagnostic apparatus comes to be one of essential imaging modalities. Because the ultrasonic diagnostic apparatus has its superiority in that the apparatus is comparatively small in size and inexpensive, free of X-ray exposure, and enables blood flow imaging using an ultrasonic Doppler technique.

In particular, in recent years, attention has been paid to a tissue harmonic imaging technique for sampling and imaging a harmonic component (such as a second harmonic component, for example) that is a non-fundamental component of a transmission ultrasonic wave produced by non-linear propagation of tissues relevant to an ultrasonic wave. This technique is advantageous in that a harmonic component is extracted, and transmission beams can be emitted more finely, a side lobe can be reduced, and further, a high quality image can be produced.

In addition, there is known a harmonic imaging technique utilizing non-linearity of an ultrasonic contrast medium concerning ultrasonic reflection, thereby acquiring dynamic information on blood flow. The non-linearity of a contrast medium is stronger than that of tissues of a living body. Thus, a harmonic component of a transmission ultrasonic wave is sampled from a receiving echo, and is imaged, thereby making it possible to generate an image with a better contrast between a tissue and the contrast medium.

In the harmonic imaging, a filter is used to sample a harmonic component. However, in actuality, with respect to the fundamental component and harmonic component of a transmission ultrasonic wave contained in a receiving echo, substantial parts of frequency ranges are superimposed on each other on a frequency axis as shown in FIG. 12. Thus, there is a problem that the fundamental component and harmonic component cannot be separated expectedly even using the filter. Namely, if an attempt is made to sample only a harmonic component, a cutoff frequency of the filter must be set to $f_{high}$. By setting this, the harmonic component is narrow in bandwidth, the resolution in an image depth direction is degraded, and signal intensity is lowered as well. In contrast, when such cutoff frequency is set to $f_{low}$ in the figure, a harmonic component in a wide bandwidth can be sampled, however, a large amount of fundamental components coexist. Thus, an increase amount of artifacts such as side lobe of the fundamental appear on an image.

In such a dilemma, in recent years, there has been known an imaging technique called a pulse inversion technique in the publication "Non-linear Propagation of Ultrasonic Pulses, Tomo-o Kamakura, et al., (Report of The Institute of Electronics & Communication Engineers US 89-23, p. 53). This pulse inversion technique is a technique that: individually transmits two ultrasonic waves, which their polarities is inverted to each other, for every scanning line for forming one image; and adds RF or IQ data, which is derived from transmission of one of the two ultrasonic waves having a non-inverted polarity, to RF or IQ data, which is derived from transmission of the other of the two ultrasonic waves having an inverted polarity, thereby producing image data for one frame.

According to this pulse inversion technique, in the case of a static scatterer and reflecting echo source, only a harmonic component can be sampled from frequency ranges superimposed on a fundamental component by the addition. That is, a harmonic component in a wide bandwidth can be sampled.

However, in the case of that a living body is a diagnostic subject, it is impossible to avoid movements of viscera. In the case of using the pulse inversion technique, it is impossible to exhibit the function of the elimination of the fundamental component by the addition. The fundamental component remains. And this remainder component appears on an image as a motion artifact.

According to this pulse inversion technique, although it is required to generate an ultrasonic pulse having its positive and negative polarities completely inserted from its principle of operation, such pulse generation is technically difficult in actuality. Therefore, even if the described motion of a living body is almost ignored, the remaining component of the fundamental component caused by addition occurs, and thus, the fundamental component cannot be completely or fully separated from the harmonic component.

SUMMARY OF THE INVENTION

The present invention has been made in view of the described circumstances in the prior art. It is an object of the present invention to provide an ultrasonic diagnostic apparatus and an ultrasonic imaging method for broadening a bandwidth of a harmonic component provided for image generation, thereby improving the resolution signal intensity of a beam depth resolution, and generating a harmonic image obtained by restraining an occurrence of a motion artifact on an image, thereby providing information useful for diagnosis.

In order to achieve the foregoing object, according to one aspect of the present invention, an ultrasonic diagnostic apparatus is directed to an apparatus for scanning a subject with ultrasonic pulses, the apparatus comprising: a transmission means for transmitting the ultrasonic pulses to each scanning line of the scan a plurality of times; a receiving means for receiving an ultrasonic echo signal returned when the ultrasonic pulses are reflected or scattered in the subject, and acquiring an electrical receiving signal that corresponds to the ultrasonic echo signal; a filter means for applying filter processing with characteristics that are different depending on a respective one of the plurality of receiving signals each corresponding to the ultrasonic echo signal; a synthesizing means for synthesizing the plurality of receiving signals processed by this filter means; a generating means for generating an image using the receiving signals synthesized by this synthesizing means; and a display means for displaying the image generated by this generating means.

As a preferred embodiment, the ultrasonic pulses transmitted by the transmission means are different from each other at its center frequency every time repeated transmission relevant to each scanning line is carried out. In addition, according to another example, the ultrasonic pulses transmitted by the transmission means has a narrow frequency bandwidth to an extent such that the signal component corresponding to the harmonic component of the ultrasonic pulse can be easily separated from the signal component that corresponds to the fundamental component. In this case, the synthesized signal components each corresponding to the harmonic component has a wider bandwidth than the bandwidth of the harmonic component obtained by one transmission/receiving and filter processing of the ultrasonic pulse.

According to still another embodiment, the filter means is a means for sampling from the receiving signal the signal component corresponding to the harmonic component of the ultrasonic pulse.

For example, the harmonic component is a signal component that corresponds to a second harmonic component of the ultrasonic pulses generated by the non-linearity of physiological tissues of the subject. In addition, for example, the harmonic component is a signal component that corresponds to the second harmonic component or sub-harmonic component of the ultrasonic pulses generated by the non-linear behavior of an ultrasonic contrast medium administered to the subject.

Further, as an example, the filter may be a means for executing filter processing with characteristics in which the fundamental component of the ultrasonic pulses remains positively in a predetermined amount. In addition, the filter means may be a means for executing filter processing for sampling a plurality of the harmonic components.

Further, in the previously described ultrasonic diagnostic apparatus with its basic configuration, the filter means may be a means for changing filter characteristics of the filter processing according to the depth of such each scanning direction. In addition, the filter means may have a filter composed of complex coefficients for carrying out the filter processing. Further, for example, a synthesizing process carried out by the synthesizing means is a process for adding the plurality of receiving signals.

Further, in the previously described ultrasonic diagnostic apparatus having its basic configuration, it is desirable that the transmission means comprises means for changing at least one parameter of the center frequency and frequency bandwidth of the ultrasonic pulses every time the ultrasonic pulses are repeatedly transmitted to such each scanning line a plurality of times, the amplitude of the ultrasonic pulses, aperture during transmission of the ultrasonic pulses, a focus when the ultrasonic pulses are focused in a beam shape, and a receiving gain relevant to the receiving signal.

Further, in the previously described basic configuration, another filter means for applying another filter processing to the receiving signal synthesized by the synthesizing means can be further provided.

Further, in the previously described basic configuration, the ultrasonic pulses transmitted by the transmission means each have a frequency bandwidth in which a signal component corresponding to the harmonic component of the ultrasonic pulses and a signal component corresponding to its fundamental component are partially superimposed on each other on spectra in the receiving signal. In this case, for example, it is desirable that the filter means is a means for sampling from the receiving signal a signal component of its frequency range that is not superimposed with the fundamental component on spectra, of the signal components each corresponding to the harmonic component.

Further, in the previously described basic configuration, the transmission means may be a means for changing the count of plural transmissions of the ultrasonic pulses and the level of the center frequency in each transmission of the ultrasonic pulses so that physiological attenuation is corrected at the receiving signal synthesized by the synthesizing means.

Further, according to another aspect of the present invention, there is provided an ultrasonic diagnostic apparatus comprising: a transmission means for transmitting ultrasonic pulses to each scanning line of a scan a plurality of times; a receiving means for receiving an echo signal returned when the ultrasonic pulses are reflected or scattered in the subject, and obtaining an electrical RF signal that corresponds to the ultrasonic echo signal; a filter means for applying filter processing with characteristics that are different depending on a respective one of the plurality of RF signals received by the receiving means to such each scanning line; a synthesizing means of synthesizing a plurality of harmonic signals processing by this filter means; a generating means for generating an image signal from the harmonic signal synthesized by this synthesizing means; and a display means for displaying the image signal generated by this generating means as the image. For example, the synthesized harmonic signals each have a bandwidth wider than that of the harmonic component obtained by one transmission/receiving and filter processing of the ultrasonic pulses.

Further, according to another aspect of the present embodiment, an ultrasonic diagnostic apparatus is directed to an apparatus for scanning a subject with ultrasonic pulses, thereby obtaining a harmonic image, the apparatus comprising: a transmission means for transmitting the ultrasonic pulses having narrow-bandwidth spectrum characteristics a plurality of times to an extent such that a signal component corresponding to a harmonic component can be easily separated from a signal component that corresponds to its fundamental component with respect to each scanning line of the scan; a receive processing means for receiving the echo signal of the ultrasonic pulses over the plural times of transmissions, thereby forming a harmonic signal having a wide-bandwidth spectrum characteristics; and an image generating means for generating the harmonic image from this harmonic signal.

With this configuration, as an example, it is desirable that, in the ultrasonic pulses transmitted by the transmission means, its center frequency is different every time transmission is repeatedly carried out for each scanning line. In addition, it is desirable that the signal processing means comprises a filter means for sampling the signal component that corresponds to the harmonic component of the ultrasonic pulses every such transmission and a synthesizing means for mutually synthesizing a plurality of signal components every such transmission.

On the other hand, an ultrasonic imaging method according to the present invention is characterized in that: transmission of ultrasonic pulses, receiving of an echo signal, and acquisition of a receiving signal are executed a plurality of times for each scanning line of a scan; filter processing with characteristics that are different depending on a respective one of a plurality of receiving signals to be received is applied to each scanning line; the plurality of processed receiving signals are synthesized with each other; the image is generated by using the synthesized receiving signal; and then, this image is displayed.

For example, the transmitted ultrasonic pulses are different from each other at its center frequency every time transmission is repeatedly carried out for each scanning line. In addition, it is desirable that the transmitted ultrasonic pulse has a narrow frequency bandwidth to an extent such that a signal component corresponding to the harmonic component of the ultrasonic pulses in a receiving signal can be easily separated from a signal component corresponding to its fundamental component. In this case, a signal component corresponding to the thus synthesized harmonic component is characterized by having a bandwidth that is wider than that of the harmonic component obtained by one transmission/receiving and filter processing of the ultrasonic pulses. In addition, filter processing is a process for sampling from a receiving signal a signal component that corresponds to the harmonic component of ultrasonic pulses every transmission. Further, for example, the harmonic component is a second harmonic component of ultrasonic pulses generated by the non-linearity of physiological tissues of a subject or a second harmonic component of ultrasonic pulses generated by the non-linear behavior of the ultrasonic contrast medium administrated to the non-linearity of the physiological tissues of the subject.

Further, according to a preferred embodiment, transmission denotes changing at least one parameter of at least one of the center frequency and frequency bandwidth of the ultrasonic pulses; a bandwidth of the ultrasonic pulses; aperture during transmission of the ultrasonic pulses; a focus when the ultrasonic pulses are focused in a beam shape; and a receiving gain relevant to the receiving signal every time the ultrasonic pulses are repeatedly transmitted to such each scanning line a plurality of times.

In this manner, a wide-bandwidth harmonic component that cannot be obtained by one transmission can be reliably acquired, whereby penetration is improved; and an occurrence of the remains of the fundamental component caused by a body motion or the incompleteness of differential. In this manner, there can be provided a harmonic image produced by preventing an occurrence of an artifact.

According to another aspect of the present embodiment, there is provided an ultrasonic diagnostic apparatus comprising: a transmission means for transmitting ultrasonic pulses having their two polarities inverted each other for each scanning line in which ultrasonic pulses are to be scanned; a receiving means for acquiring an electrical receiving signal that corresponds to an ultrasonic echo returned when the ultrasonic pulses are reflected or scattered in the subject every such transmission; a synthesizing means for synthesizing the plurality of receiving signals so as to widen the bandwidth of a harmonic component relevant to the fundamental component of the ultrasonic pulses; and an image generating means for generating a harmonic image from the harmonic component widened in bandwidth by the synthesizing means.

For example, it is desirable that the synthesizing means comprises: a means for adding a receiving signal with its inverted polarities in the fundamental component of the ultrasonic pulses, thereby sampling the harmonic component; and a means for synthesizing the thus sampled harmonic component.

As has been described above, according to ultrasonic imaging of the present embodiment, ultrasonic pulses are transmitted to each scanning line by changing characteristics a plurality of times, for example; filter processing with its different characteristics is applied to a respective one of a plurality of the thus received receiving signals; a plurality of the filter-processed receiving signals are synthesized; and the synthesized receiving signals are used so as to generate/ display an image. Thus, a wide-bandwidth harmonic signal provided for image generation is generated; the resolution and SNR in a depth direction are improved; and an occurrence of a motion artifact caused by a motion of tissues is significantly decreased. In this manner, there can be provided a useful harmonic image having high image quality and excellent depicting capability while maintaining high penetration.

A specific configuration and characteristics according to another aspect of the present invention is clarified by embodiments of the invention and accompanying drawings described below.

BRIEF DESCRIPTION OF THE DRAWINGS

In the accompanying drawings,

FIG. 3 is a view illustrating spectra of a fundamental component for each rate;

FIG. 4 is a view illustrating spectra of a harmonic component generated for each rate;

FIG. 5 is a view illustrating filter characteristics for each rate;

FIG. 9 is a view schematically illustrating combination of a sub-harmonic component according to one modified example;

FIG. 10 is a spectrum chart of a harmonic component illustrating a synthesizing process of another modified example;

DETAILED DESCRIPTION OF PREFERRED EMBODIMENTS

Hereinafter, preferred embodiments of the present invention will be described with reference to the accompanying drawings.

(First Embodiment)

A harmonic imaging ultrasonic diagnostic apparatus according to a first embodiment will be described with reference to FIG. 1 to FIG. 8 and FIG. 11.

Figure 1:
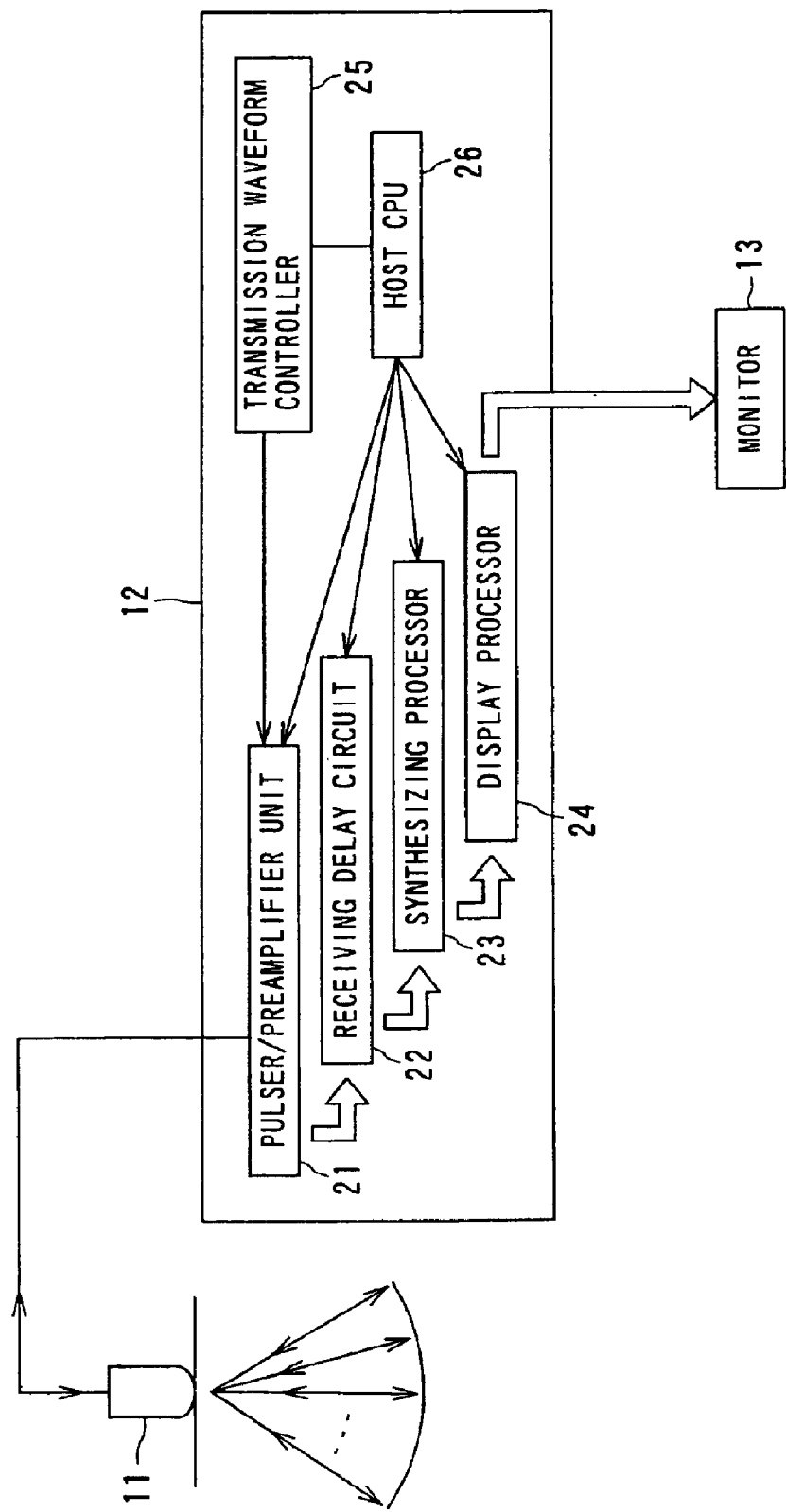
FIG. 1 is a block diagram depicting a schematic configuration of an ultrasonic diagnostic apparatus according to one embodiment of the present invention.

This ultrasonic diagnostic apparatus, as shown in FIG. 1, comprises: an ultrasonic wave transmission/receiving probe 11; a main body 12 connected to this probe, the main body driving this probe and generating harmonic image data; and a monitor 13 for displaying the harmonic image data generated by the main body 12.

The probe 11 preferably comprises an arrayed oscillators arranged in a one-dimensional or two-dimensional manner.

The main body 12, as shown, comprises a pulser/preamplifier unit 21, a receiving delay circuit 22; a synthesizing processor 23, a display processor 24, a transmission waveform controller 25, and a host CPU 26. Although not shown, a memory having recorded therein a program representing the procedures is connected to the host CPU 26. In addition, the circuits and processors 21 to 25 each incorporates a memory for recording a program representing these procedures (not shown) as required.

The pulser 21 supplies a drive voltage to a probe 11, drives the probe, and controls a delay time of a drive voltage applied to a plurality of arranged transmitters. An ultrasonic signal is generated from an transmitter of the probe 11 driven by this drive voltage, and beam formed by a delay control. The ultrasonic beams are controlled to be directed/focused in a two-dimensional direction or three-dimensional manner.

The transmission waveform control 25 is provided for controlling an operation of the pulser 21. Specifically, the pulser 21 is controlled so as to generate ultrasonic pulses of a plurality of waveforms set independently relevant to each scanning line of a plurality of scanning lines each configuring an image of one frame. Namely, ultrasonic pulses having their different characteristics (such as bandwidth) are transmitted respectively from the probe 11 over a plurality of rates (for example, two rates: refer to FIG. 11) in a time series direction, under the control of a transmission waveform controller 25.

The ultrasonic pulse signal transmitted in a living body generates a harmonic signal with propagation of ultrasonic pulses due to the non-linearity of physiological tissues. Namely, an ultrasonic signal consisting of the fundamental and non-fundamental components is reflected at a boundary of acoustic impedance of body internal tissues, and/or backwardly scattered by very small scattering elements in the body. This ultrasonic signal is received by the same probe 11, and is converted into a receiving signal of a voltage quantity. This receiving signal is amplified in advance by means of a preamplifier 21, and the amplified signal is delivered to a receiving delay circuit 22.

The receiving delay circuit 22 executes a so called digital type receiving process in which the receiving signal is amplified in advance, and the amplified signal is A/D converted before phasing/adding immediately after being amplified. This digitizing process may be a so called analog type receiving process to be carried out after phasing/adding.

Further, the receiving delay signal 22 phases/adds a receiving signal, and delivers the phased/added signal to a synthesizing processor 23. By the phasing/adding, beam forming during reception is carried out by computation, and the direction/focusing of the receiving signal is controlled.

The receiving delay circuit 22 can have a plurality of paired receiving delay circuits, thereby forming a plurality of beam-shaped receiving signals so as to carry out parallel, simultaneous receiving.

The synthesizing processor 23 is a means that applies filter processing according to a spectrum waveform of a receiving signal, samples a harmonic component from receiving signals of a plurality of rate relevant to each scanning line, and synthesizes these sampled signals. A harmonic image characterized in the present invention is generated through such sampling process and synthesizing process.

Figure 2:
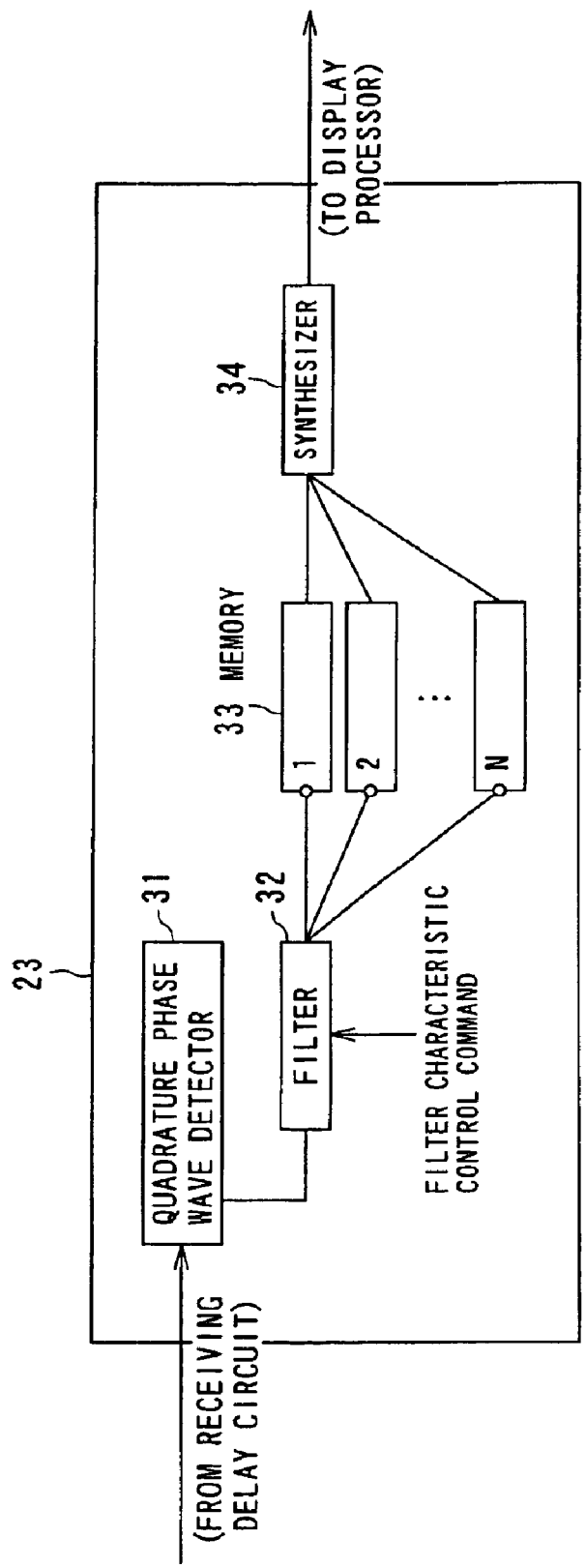
FIG. 2 is a block diagram depicting a schematic configuration of a synthesizing processor.

In detail, the synthesizing processor 23 is configured as shown in FIG. 2. That is, the synthesizing processor 23 has a quadrature phase wave detector 31 for inputting a receiving beam signal outputted from the receiving delay circuit 22, and has a filter 32, a plurality of memories 33 ($33_1$ to $33_N$), and a synthesizer 34.

In the case of a configuration that carries out the described parallel simultaneous receiving, it is preferable that the synthesizing processor 23 has a processor circuit that corresponds to the number of parallel simultaneous receptions so that the processor may be formed so as to composite receiving signals in number corresponding to the number of parallel simultaneous receptions at the same time. Although the synthesizing processor 23 represents in block or functionally a synthesize processing section for one channel in a plurality of channels to be received in parallel and simultaneously, in the case of a configuration for carrying out parallel simultaneous receiving, such synthesize processing section is provided by a plurality of channels (not shown).

A quadrature phase wave detector 31 wave-detects an inputted beam shaped receiving signal in a quadrature phase by means of a reference signal of a reference frequency $F_0$, and forms a complex signal. It is preferable that this reference frequency $F_0$ be set to a gravity frequency of a composite harmonic component described later. This wave detecting signal is delivered to a filter 32.

The filter 32 applies filter processing of transient characteristics that are different depending on each rate according to a difference in characteristics (such as bandwidth) of ultrasonic pulses transmitted at each rate, and stores the filtering result in a memory 33 ($33_1$ to $33_N$) for each rate. This filter 32 is composed of a complex coefficient filter. This filter is a digital type capable of changing filter characteristics according to the depth in a scanning line direction. A command for controlling the filter characteristics is assigned from a host CPU 26, for example.

The memory 33 does not always need to be composed of a plurality of memory devices for storing the filtering result for each rate, as shown in FIG. 3, and may be composed of one memory devices. In this case, the filtering results for each rate may be sequentially synthesized, and a memory configuration is simplified.

The synthesizer 34 synthesizes the filtering results of each rate stored in memory 33 ($33_1$ to $33_N$), and further, applies required processing such as algorithmic compression, thereby converting them into luminance values of image display. The signal synthesized by this synthesizer 34 is delivered to a display processor 23 as an image signal of one transmission/receiving scanning line.

The composite receiving signals synthesized by this synthesizing processor 23 are delivered sequentially to the display processor 23 for each rate. The display processor 24 has a function for scanning/converting a composite receiving signal, and generating an image signal by means of a built-in digital scan converter. In this manner, the scanned/converted signal is delivered to the display monitor 13 as an image signal, and is displayed as a harmonic image according to the present invention.

The host CPU 26 equipped with the main body 12 is configured so as to entirely control an operating timing of the described processor or circuit.

(Advantageous Effect of the Present Embodiment)

Now, an operation of an ultrasonic diagnostic apparatus according to the present embodiment will be described by focusing on transmission waveform control, filter processing, and synthesize processing.

Assume that two transmissions are carried out for a respective one of the scanning lines each forming a two-dimensional scan plane or a three-dimensional scan region. The transmission waveform controller 25 controls a pulse 21, wherein ultrasonic pulses of the basic base components $WF_{41}$ and $WF_{42}$ having mutually different frequency characteristics (spectra) ($WF_{41} < WF_{42}$ at center frequency) are transmitted to be divided into two rates, respectively, relevant to each of the scanning lines, as shown in the waveforms of FIG. 3A and FIG. 3B.

Figure 13:
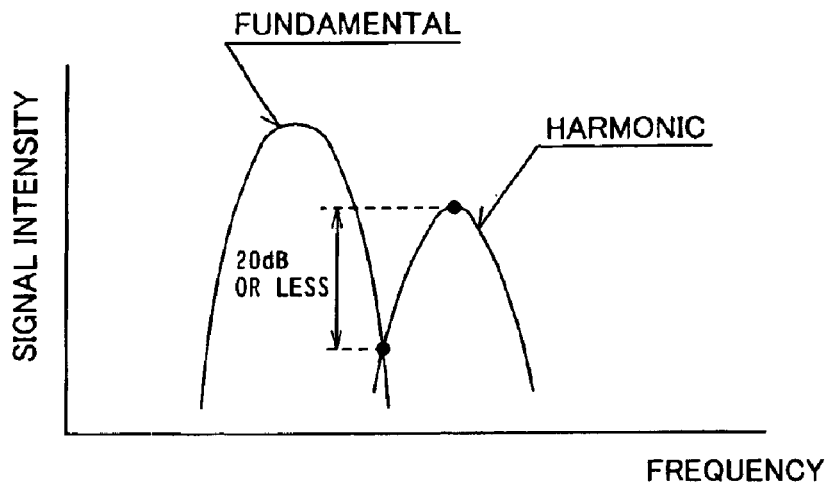
FIG. 13 is a spectrum chart illustrating a degree of a narrow bandwidth of ultrasonic pulses to be transmitted.

The frequency characteristics are set in a narrow bandwidth to an extent such that a harmonic component included in a receiving signal can be easily sampled/divided from a fundamental component, as shown in FIG. 5 described later. The degree of bandwidth narrowing according to the present invention specifically denotes a range in which a region where a fundamental component and a harmonic wave component are superimposed on frequency spectra is lower by about 20 dB as compared with a peak of the harmonic wave, as shown in FIG. 13.

Figure 11:
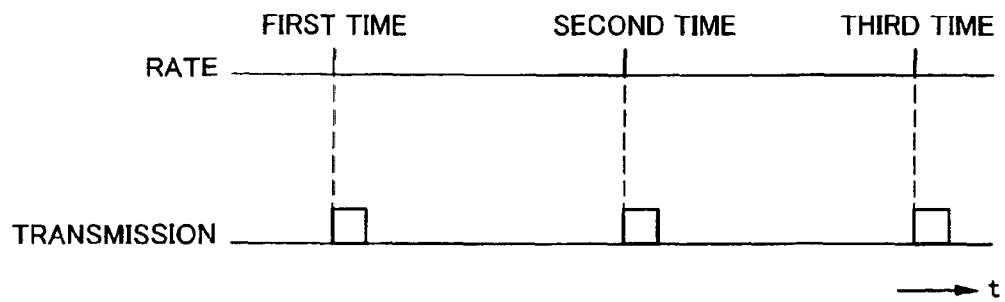
FIG. 11 is a view illustrating a rate and a transmission timing.
Figure 12:
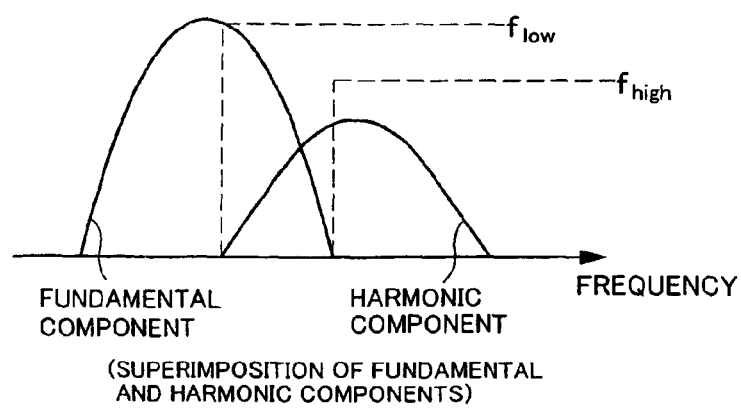
FIG. 12 is a spectrum view illustrating a state in which separation properties of a fundamental component and a harmonic component for illustrating a conventional example is low.

In this manner, an ultrasonic pulse having a fundamental component $WF_{41}$ is transmitted from the probe 11 at a first rate shown in FIG. 11 (during transmission in response to a first rate pulse), and an ultrasonic pulse having a fundamental component $WF_{42}$ is transmitted at a next rate (during transmission in response to a second rate pulse).

When these ultrasonic pulses are transmitted, respectively, from the probe 11 into a subject, a harmonic component of the ultrasonic pulses is generated by non-linear characteristics relevant to ultrasonic propagation in a living body. Thus, the ultrasonic echoes of these ultrasonic pulses each include a fundamental and a harmonic components (here, referred to as a second harmonic component), as shown in FIG. 4A and FIG. 4B. Namely, at a first rate, a fundamental component $WF_{41}$ and its harmonic component $WF_{51}$ are included, and at a second rate, the fundamental component $WF_{42}$ and its harmonic component $WF_{52}$ are included.

In this case, the bandwidth of the ultrasonic pulses transmitted at each rate is set in a narrow bandwidth. Thus, as shown in FIG. 4, a bandwidth between the fundamental component $WF_{41}$ at the first rate and its harmonic component $WF_{51}$ is reliably separated up to a predetermined signal level. On the other hand, a bandwidth between a fundamental component $WF_{42}$ at a second rate and its harmonic component $WF_{52}$ is reliably separated up to a predetermined signal level.

Here, although only the most powerful second harmonic component is shown as a typical component of a non-fundamental component, in actuality, a harmonic component such as a third harmonic component or a sub-harmonic component is included. In addition, an ultrasonic contrast medium for casing ultrasonic waves to be scattered in a nonlinear manner is administered to the inside of a subject. In the case of scanning a site at which such a contrast medium exists, a more powerful harmonic component is obtained from the contrast medium as compared with the harmonic component produced by the nonlinear propagation properties of a living body.

The ultrasonic echo signal including the described fundamental component and harmonic component is received by the probe 11 for each rate, and is outputted as a receiving signal. Then, the receiving signal is amplified by means of a preamplifier unit 21, the amplified signal is subjected to receiving beam forming by means of the receiving delay circuit 22, and the beam formed signal is focused on a beam on a scanning line. This beam formed receiving signal is further subjected to quadrature phase wave detection by using a reference signal in the synthesizing processor 32. The phase wave detected signals at a real part and an imaginary part are delivered to the filter 32.

In the filter 32, as shown in FIG. 5A, a passing bandwidth $B_{61}$ is automatically set so that the center frequency at the first rate passes a harmonic component $WF_{51}$ that is lower than that of the second rate. Next, at the second rate, as shown in FIG. 5B, the passing bandwidth $B_{62}$ is automatically set so that the center frequency passes a harmonic component $WF_{52}$ that is higher than that of the first rate.

That is, at each rate, the passing bandwidth is optimally set according to a reference frequency used for quadrature phase wave detection and a bandwidth owned by a harmonic to be sampled. In this setting, although the amplitude characteristics of the filter 32 can be set independently for each rate, it is important that the phase characteristics are identical at each rate.

As shown in FIG. 4 and FIG. 5, a fundamental component and a harmonic component are reliably separated from each other up to a predetermined signal level, and thus, these passing bandwidths $B_{61}$ and $B_{62}$ (including a cutoff frequency) can be easily designed.

Figure 6A:
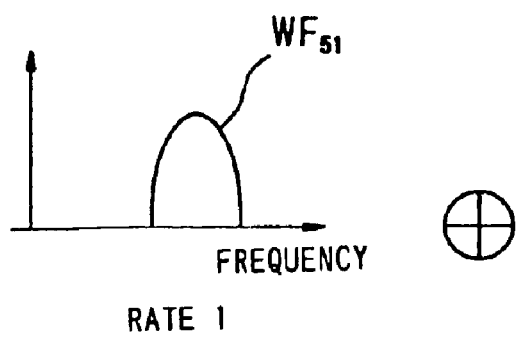
FIG. 6 is a view schematically illustrating a synthesizing process of a harmonic component.
Figure 6B:
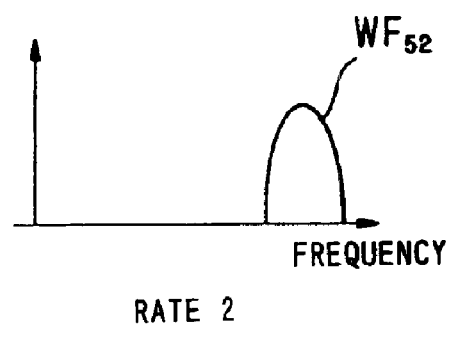

Then, the basis wave component $WF_{41}$ ($WF_{42}$) is eliminated for each rate by means of the filter 32, and as shown in FIG. 6A and FIG. 6B, the harmonic component $WF_{51}$ ($WF_{52}$) is reliably sampled. These harmonic components $WF_{51}$ and $WF_{52}$ are stored, respectively, in memories $33_1$ and $33_2$ that are different from each other for each rate.

Figure 6C:
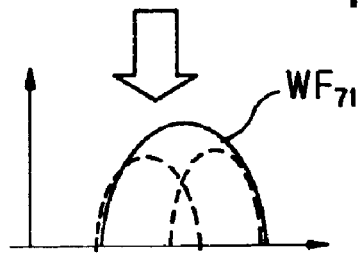

In the synthesizing processor 32, further, the signal values of each rate stored in memories $33_1$ and $33_2$ are synthesized by means of the synthesizer 34 in accordance with an additive computation approach, for example. A concept of this composition is shown in FIG. 6C. By thus synthesizing these signal values, a wide-bandwidth harmonic component $WF_{71}$ obtained by adjusting the harmonic components $WF_{51}$ and $WF_{52}$ that have been narrow in bandwidth on a frequency axis to be equal to each other is generated.

Further, an imaging process such as logarithmic compression is properly applied to the thus synthesized band-width signal by means of the synthesizer 34, and a display processor 24 is delivered as an image signal of one scanning line.

The above-mentioned operations are sequentially executed for each scanning line for forming a two-dimensional scan plane or a three-dimensional scan region. Namely, in the case where a harmonic component to be composed as in the present embodiment is by two rates, an image signal of a first scanning line is generate at two rates, i.e., the first and second rates, and an image signal of the second scanning line is generated at two rates, i.e., the next third and fourth rates, and an image signal of the third scanning line is generated at two rates, i.e., the fifth and sixth rates. Then, an image signal relevant to a predetermined number of scanning lines is generated similarly, and the generated signal is delivered to the display processor 24.

To the display processor 24, image signals relevant to a predetermined number of scanning lines are also delivered from the remaining channels of the parallel simultaneous receiving process channel processed in the same way as described above. Thus, when the image signals of all the scanning lines are ready, the display processor 24 scans/converts these image signals, delivers them to the monitor 13, and display an image in a scan region.

As has been described above, according to this ultrasonic diagnostic apparatus, the ultrasonic pulse transmitted each time has a narrow bandwidth in which the fundamental and the harmonic components can be easily identified, and thus, the filter 32 can samples only the harmonic component reliably. Therefore, high precision sampling of harmonic components is carried out to an extent such that the fundamental component included in the sampled harmonic component can be ignored.

The resultant harmonic components produced by a plurality of transmissions are mutually composed, and are formed as a wide-bandwidth harmonic component, as shown in FIG. 6C. By widening a bandwidth due to this post-processing, the resolution in the depth direction of a scanning line is improved, and signal intensity rises, thereby resulting in the improvement of the SNR (Signal/Noise Rate). can be improved. In addition, because of transmission in a narrow bandwidth, a signal itself is excellent in penetration, and a signal after synthesized is further improved.

In addition, according to harmonic imaging of the present embodiment, the described wider bandwidth and high penetration are compatible with each other (hereinafter, referred to as "depth when an ultrasonic signal of a minimum energy that the apparatus can detect"). According to a conventional pulse inversion technique, in order to widen a harmonic component in bandwidth, the fundamental component itself must be set in a wide bandwidth. Thus, it has been necessary to accept lowering of penetration. In contrast, in the case of an apparatus according to the present embodiment, the transmission itself of ultrasonic pulses is carried out in a narrow bandwidth, and thus, the apparatus is advantageous in view of penetration as compared with a pulse inversion technique.

Namely, in the case of the pulse inversion technique, when the resolution in the depth direction is constant, penetration is determined depending on a maximum voltage of an ultrasonic pulse that can be outputted by the apparatus. In contrast, in the case of harmonic imaging according to the present embodiment, the continuous wave length is increased (namely, a narrow bandwidth is obtained). In this manner, penetration can be improved even at the same maximum voltage.

Further, according to the present embodiment, the fundamental component on the scanning line is eliminated at a filter for each rate. Thus, even if a motion of tissues exists, the fundamental component can be reliably eliminated, and there cannot occur a motion artifact caused by the remains of the fundamental component on an image of harmonic imaging. In the case of a conventional pulse inversion technique, the remains of the fundamental component occurs due to an effect of a motion of tissues, which causes an artifact. However, in the present embodiment, such a circumstance can be reliably eliminated.

Furthermore, in the case where a parallel simultaneous receiving process is employed in the apparatus according to the present embodiment, real time properties are improved. Thus, even in the case where a plurality of transmissions (for example, two transmissions as described above) are required for generating an image signal in one scanning line, the lowering of real time properties due to such plurality of transmissions can be compensated for.

In this way, according to the present embodiment, a variety of advantageous effects are achieved. What is particularly emphasized is that a harmonic component with a purely wide bandwidth obtained by filter processing and synthesize processing as post-processing is not obtained by only one transmission, and is obtained by being carried out as described above. As has been described previously, in the case of transmitting a fundamental component in a wide bandwidth, only one transmission is carried out, however, this fundamental component cannot be separated by means of a filter because the spectra of the fundamental component and harmonic component are superimposed on each other. On the other hand, in the case of a pulse inversion technique (two transmissions), a motion artifact occurs. In contrast, by carrying out the present invention, there is provided a significant advantageous effect that cannot be achieved by the conventional technique in that these problems are solved at the same time.

Figure 7A:
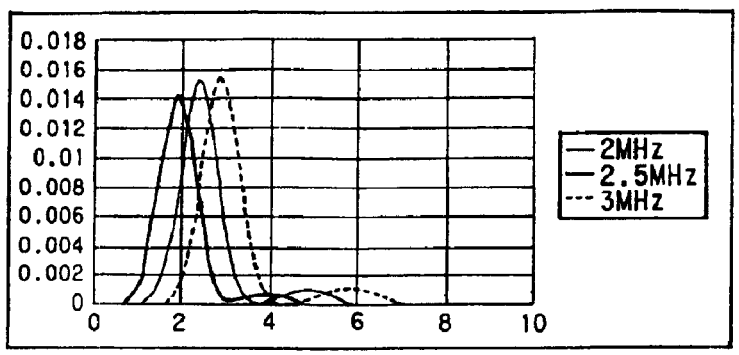
FIG. 7 is spectrum chart showing the result of simulation.
Figure 7B:
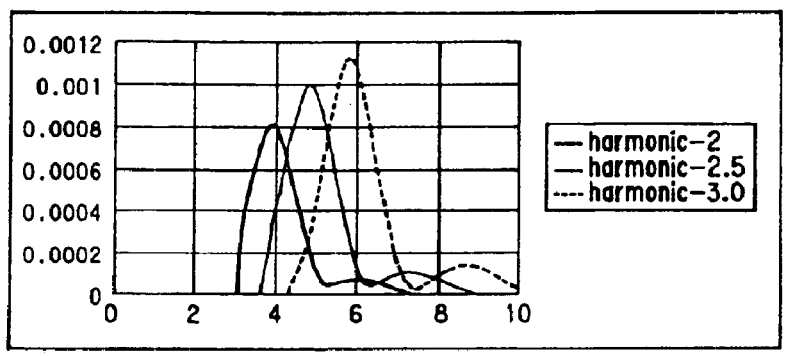
Figure 7C:
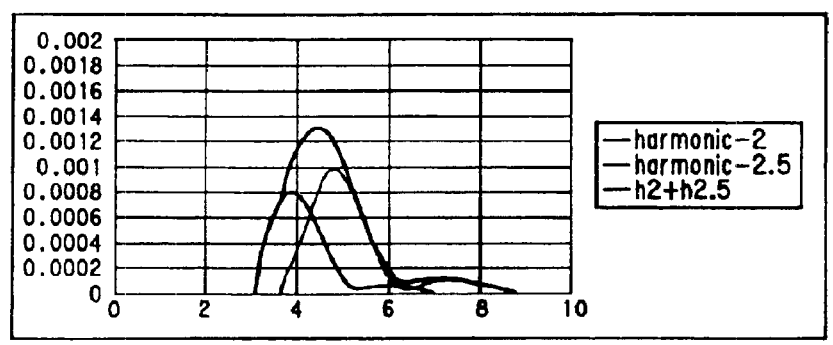
Figure 7D:
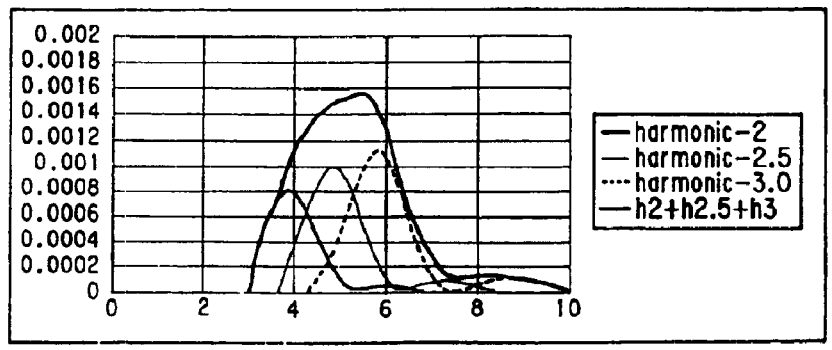

The Inventor carried out simulation of composition of pulse waveform propagation in a focused sound field by using a differential approach to solve a KZK equation for parabola approximation, describing nonlinear propagation (refer to Basics of Study of Nonlinear Acoustics, Tomoo Kamakura, Aichi Shuppan) in order to verify an effect of the present invention based on the described principle of operation. The result is shown in FIG. 7. FIG. 7A shows the result of simulation of spectra (amplitude) caused when the Gausian waveforms (fundamental components) whose center frequencies are 2 MHz, 2.5 MHz, and 3 MHz are propagated separately in water. FIG. 7B shows spectra when harmonic components of three types of fundamental components of 2 MHz, 2.5 MHz, and 3 MHz are sampled separately. FIG. 7C shows spectra when harmonic components of two types of fundamental components of 2 MHz and 2.5 MHz are added. Similarly, FIG. 7D shows spectra when harmonic components of three types of fundamental components of 2 MHz, 2.5 MHz, and 3 MHz are added. From these added spectra, it is verified that the signal intensity increases, and a bandwidth is widened.

Further, although not shown, in this simulation, it is verified that the phase of a respective harmonic component connects linearly other than a jump of $2\pi$. In this way, all the components are to be in phase, thus making it possible to widen a bandwidth by means of a synthesizing process. As a filter, there is employed a filter whose phase characteristics are equal to each other at the same frequency, and whose amplitude characteristics are independent of each other.

Figure 8A:
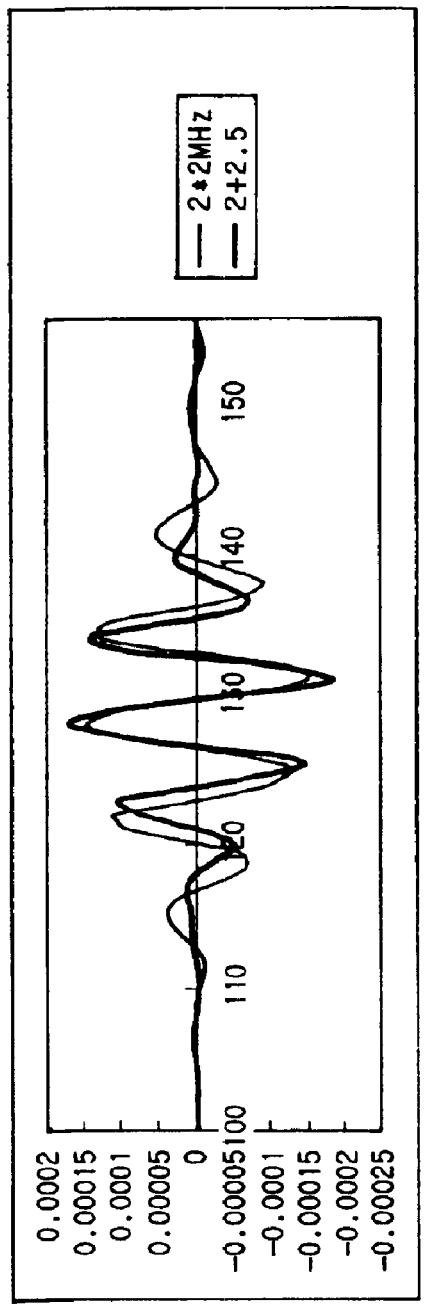
FIG. 8 is a waveform chart showing the result of simulation.
Figure 8B:
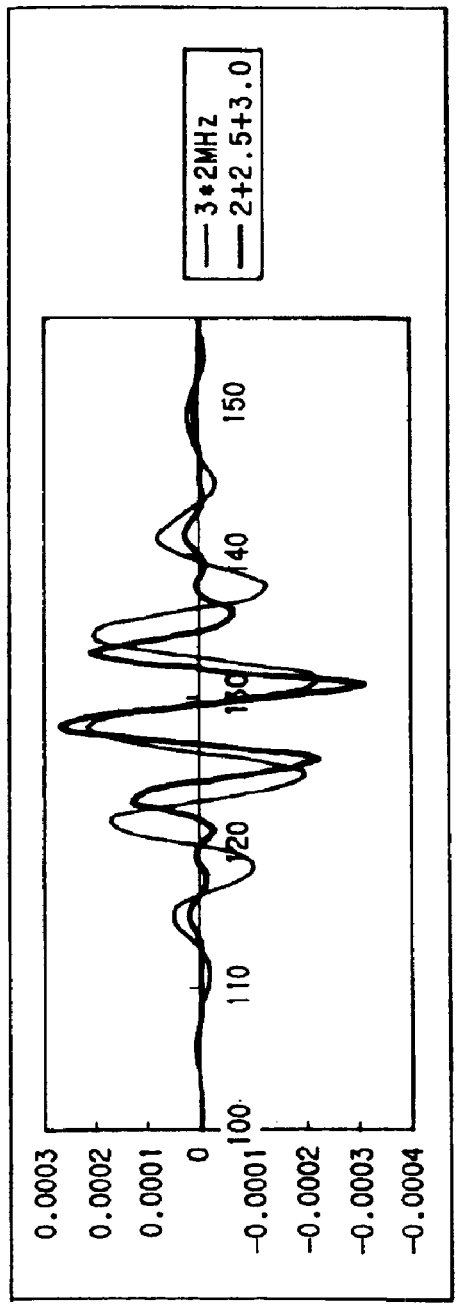

Further, in simulation shown in FIG. 8 executed by the Inventor, the waveforms obtained by adding harmonic components of 2 MHz and 2.5 MHz and a waveform obtaining by doubling the bandwidth of 2 MHz harmonic components are obtained. These waveforms are shown in FIG. 8A. In addition, a simulation for adding harmonic components of three types of 2 MHz, 2.5 MHz, and 3 MHz and a simulation for tripling the amplitude of a harmonic component of 2 MHz are carried out, and the waveforms of these components are shown in FIG. 8B. From these simulation waveforms as well, it is found that the signal intensity is increased, and the continuous wavelength is reduced to widen the bandwidth by means of composition as compared with a case where a mere amplitude is amplified.

(Modified Example)

Further, the described embodiments can be carried out by modifying them into a variety of modes.

A first modified example relates to a configuration of a synthesizing processor 23. In this synthesizing processor 23, one quadrature phase wave detector 31 may be provided at an output side of a filter 32. In addition, this quadrature phase wave detector 31 may be provided at an output side of a synthesizer 34 (That is, configurations of the filter and synthesizer may be present before or after quadrature phase wave detection). Further, a total of two quadrature phase wave detectors 31 may be provided at an output side of the filter 32 and at an output side of the synthesizer 34.

Furthermore, in the case where the number of rates is two relevant to a plurality of transmissions per scan line, the synthesizing processor 23 may comprise a longitudinal array configuration of the quadrature phase wave detector and filter relevant to a respective one of the rates 1 and 2 in parallel, and may further comprise a longitudinal array configuration of composition processing and quadrature phase wave detection at an output side of such parallel configuration. With a variety of these configurations, a degree of freedom when the synthesizing processor is designed is increased.

As a second modified example, the number of rates relevant to a plurality of transmissions for each scanning line is not limited to 2 described above, and may be increased as required. For example, by 10 rates for each scanning line, that is, by carrying out 10 transmissions, the harmonic components of these transmissions may be sampled/added.

As another example associated with this second modified example, there can be provided a configuration considering a relationship between the transmission count for each scanning line and a physiological attenuation. In the case of a living body, as transmission at a higher frequency is carried out, the attenuation quantity when ultrasonic waves propagates the inside of a living body increases more. Thus, of a plurality of transmissions, the number of transmissions at a high frequency is increased as compared with that at a low frequency, such as one transmission at a low frequency and two transmissions at a high frequency, for example, and composition processing is carried out, whereby physiological attenuation can be corrected.

As a third modified example, the amplitude of ultrasonic pulses to be transmitted plurality of times for each scanning line may be changed for each rate, i.e., for each transmission. In this case, for example, as a higher frequency is produced, it is desirable that the amplitude of ultrasonic pulses is increased so as not to compensate for the attenuation quantity. Instead of control of this transmission amplitude, a configuration for increasing a receiving gain with an increase in frequency may be employed.

As a fourth modified example, a transmission aperture area for ultrasonic pulses to be transmitted may be changed for each rate, i.e., for each transmission, a plurality of times for each scanning line. For example, as a higher frequency is produced, the penetration decreases, and thus, the transmission aperture area is increased concurrently.

As a fifth modified example, a transmission focus of ultrasonic pulses to be transmitted may be changed for each rate, i.e., for each transmission, a plurality of times for each scanning line. For example, as a higher frequency is produced, the penetration decreases, and thus, a transmission focus is set concurrently in long distance.

A sixth modified example relates to modification of a contrast enhancement echo. In the case of imaging caused by a contrast enhancement echo technique, at a first rate, as compared with a second rate, ultrasonic pulses a short distance focus, a small aperture, and a low sound pressure are transmitted so that a harmonic echo is generated around a position of a short distance from the probe. In this manner, an effect of a sound field imparted to a contrast medium that exists at a position more distant that its short distance position can be reduced. At a second rate, transmission of a long distance focus, a large aperture, and a high sound pressure is carried out, and its harmonic echo is generated around a position of a long distance. If a contrast medium in short distance disappears during transmission of a first rate, it is assumed that penetration due to transmission at the second rate is greater. Thus, at a site in short distance, transmission at the first rate may be responsible for image generation, at a site in middle distance, transmission at both of the first and second rates may be responsible for image generation, and at a site in long distance, transmission of the second rate may be responsible for image generation.

A seventh modified example relates another example of a contrast enhancement echo. Namely, as shown in FIG. 9, this modified example relates to imaging of a sub-harmonic component as a harmonic component. According to this modified example, as shown in FIG. 9A and FIG. 9B, harmonic components $WF_{82}$ and $WF_{84}$ of fundamental components $WF_{81}$ and $WF_{83}$ caused by a contrast medium included in receiving signals at the first and second rates, respectively, are sampled by means of the filter 32. The characteristics $B_{85}$ and $B_{86}$ of the FIG. 9A and FIG. 9B are bandwidths for sampling sub-harmonic components set by this filter 32. The sampled sub-harmonic components $WF_{82}$ and $WF_{84}$ are added to each other in the same manner as described previously, and a wide-bandwidth sub-harmonic component $WF_{85}$ is generated.

The advantages achieved by using this sub-harmonic are as follows. Conventionally, in the case of obtaining a sub-harmonic component, transmission at a high frequency is generally carried out in order to the resolution in a lateral direction on a sub-harmonic image. An ultrasonic signal at a high frequency includes large attenuation in a living body, thus making it necessary to increase a burst length (that is, to narrow a bandwidth). Thus, the spatial resolution in the depth direction of a scanning line has been lowered. In contrast, in this ninth modified example, while transmitting narrow-bandwidth ultrasonic pulses that facilitate separation of a sub-harmonic component and allocation of penetration, a wide-bandwidth sub-harmonic component is finally obtained, making it possible to improve the spatial resolution in the depth direction.

An eighth modified example relates to an example of the remains of the fundamental component. That is, as described above, instead of a configuration for completely eliminating the fundamental component to the maximum, the remains of the fundamental component are produced on a harmonic image without positively completely eliminating the fundamental component. This remaining portion includes a region in which a harmonic intensity is not fully obtained at the deepest site of an image due to attenuation, or alternatively, a region in which a harmonic is insufficiently generated at a shallow region. In this manner, a site of such region is displayed by a fundamental component. In order to do this, for example, the passing bandwidth characteristics relevant to a harmonic component of the filter 32 are moved in predetermined quantity on a frequency axis according to the depth at the fundamental component side, and at the same time, the reference frequency of the quadrature phase wave detector 31 may be changed according to the depth in the same way as a conventional echo filter (as the depth increases, the reference frequency is lowered).

A ninth modified example relates to post-processing of synthesized harmonic components. In order to trim a frequency distribution of the synthesized harmonic components, a trimming filter may be added at the rear stage of the synthesizer 34. By this trimming filter, an image quality can be improved more remarkably, and the depicting capability can be improved. In addition, a configuration of this trimming process and the previously described harmonic component sampling process are mounted in advance on the previously filter 32 so that this configuration may be carried out before composition.

Further, waveform correction processing after composition processing may be executed by a filter. This filter is composed of a complex filter, an amplitude and a phase are controlled on a Fourier space independently of positive and negative frequency regions, whereby waveforms of the synthesized harmonic components are modified as required. The filter coefficient of this filter is preset by testing or simulation and the like, and, during correction, the filter coefficient is executed after read out from a table. By using this complex filter, a phase can be adjusted to coincide with another, and a waveform can be corrected more finely.

A tenth modified example relates to composition of harmonic components. In the foregoing description, a harmonic component caused by the non-linearity of propagation in a living body or a contrast medium has been schematically illustrated as spectra each having one peak in order to facilitate the understanding of the composition. However, in actuality, as shown in FIG. 10, even in the case where a distribution of fundamental components $WF_{91}$ is intense in one waveform, as indicated by a waveform $WF_{92}$, a harmonic component is generated so as to distributed in some waveforms over a wide frequency range owing to such non-linearity. This invention makes it possible to synthesize all or some arbitrary waveforms of these harmonic components that exist sparsely, and further, makes it possible to change a harmonic component to be sampled for each rate.

Further, a eleventh modified example will be described with reference to FIG. 14. This modified example relates to ultrasonic pulses to be transmitted a plurality of times.

In the previously described embodiments and their modified examples, it is presumed that narrow-bandwidth ultrasonic pulses are transmitted a plurality of times for each scanning line to an extent such that a harmonic component of an echo signal can be easily separated from its fundamental component. However, the ultrasonic pulses used in this modified example is not in a narrow bandwidth as described above, and is a comparatively wide-bandwidth pulse produced when the fundamental component and harmonic component are partially superimposed on spectra, as shown in FIG. 14.

Figure 14:
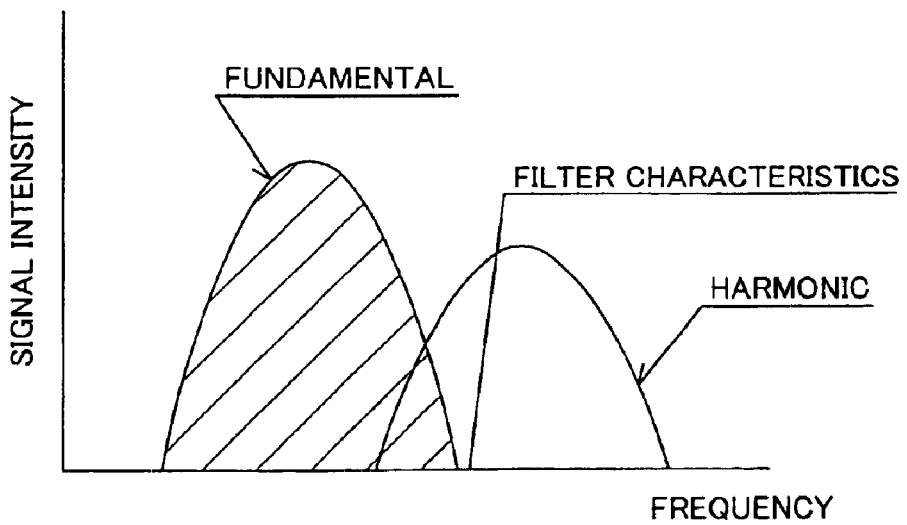
FIG. 14 is a spectrum chart of comparatively wide-bandwidth ultrasonic pulses, showing still another modified example.

In the case of using such comparatively wide-bandwidth ultrasonic pulses, as indicated by the filter characteristic curve shown in FIG. 14, the characteristics of the filter 32 of the synthesizing processor 23 may be set so as to sample a harmonic component in a frequency range free of spectrum superimposition. With respect to each scanning line, in the same way as described previously, a plurality of transmissions are carried out, a receiving signals caused by these transmissions are synthesized after they have been subjected to filter processing.

A twelfth modified example is modified into a pulse inversion technique (referred to as "phase inversion technique"), and is carried out as an application of the previously described embodiments and modified examples thereof. As described previously, in the pulse inversion technique, transmissions (two transmissions) using two ultrasonic pulses with polarities being inverted for each scanning line are carried out instead of separation of a fundamental component and its harmonic component from each other by filter processing. The resultant two receiving signals are added to each other, whereby only two fundamental components with polarities being inverted each other are eliminated according to polarity of the two ultrasonic pulses, and only two harmonic components with identical polarities are sampled irrespective of the polarities of the two ultrasonic pulses. The harmonic components sampled here are obtained by two transmissions for each scanning line, as described previously.

In contrast, in the present modified example, in the previously described embodiments and their modified examples, in particular, there is applied a composition technique for adding a plurality of receiving signals obtained by a plurality of transmissions to each other, thereby obtaining a receiving signal of a wide bandwidth. For example, scanning is performed so as to carry out transmission for each scanning line in number (for, example, four times) larger than the number (two times) based on the principle of the pulse inversion technique, and a plurality of the resultant harmonic components for each scanning line are synthesized, thereby making it possible to obtain a harmonic component of its wider bandwidth than that of such each harmonic component.

According to this modified example, even in the case of using a pulse inversion technique, a harmonic component can be broadened in bandwidth, and thus, the resolution and signal intensity in the beam depth direction can be improved as in the previously described embodiments and their modified examples. As a result, for example, advantages of the pulse inversion technique can be positively utilized, and there can be achieved an advantage that more options during device design can be chosen.

In addition, as a thirteenth modified example, an addition gain (addition coefficient) relevant to a receiving signal may be changed for each depth. In the third modified example described previously, in order to compensate for a phenomenon that, as transmission at a higher frequency is carried out, the attenuation quantity when ultrasonic waves propagate in a living body is increased more, as compared with transmission at a low frequency, a receiving gain relevant to a receiving signal obtained by transmission ultrasonic pulses may be increased as a higher frequency is produced. However, instead of this, an addition gain relevant to the receiving signal is changed for each depth.

For example, in the case where the number of transmissions for each scanning line is two (two transmissions), i.e., in the case where two transmissions are carried out at low and high frequencies, the following items are carried out. 1) The rates of receiving gain to both of the receiving signals obtained by two transmissions at high and low frequencies are equal to each other (for example, 5: 5), and the rate of addition gain is changed so as to be higher during transmission at a high frequency (for example, 6: 4); 2) The rates of receiving gain to both of the receiving signals obtained during two transmissions at high and low frequencies are changed to be higher during transmission of a high frequency with its large attenuation quantity (for example, 6: 6, thereby making it possible to equalize the rates of addition gain (for example, 5: 5).

An advantageous effect of the previously described embodiments and their modified examples is significant in the case where the present invention is applied to harmonic imaging at a low pressure sound using a contrast medium (micro-bubbles) such as Difinity or Optison called low MI (Mechanical Index) real time perfusion (tissue blood flow) imaging. In general, in low MI real time perfusion, observation is serially carried out so as not to destroy micro-bubbles under low amplitude conditions for ultrasonic pulses, and thus, penetration becomes insufficient. There is a problem that, if the number of cycles of the ultrasonic pulse is increased instead of increasing the amplitude of ultrasonic pulses in order to improve the penetration, the spatial resolution is impaired. The foregoing problem is solved by applying the present invention to low MI real time perfusion, thus making it possible to increase penetration without degradation of the spatial resolution.

In addition, in the previously described embodiments and their modified example, although a frame rate is lowered by a plurality of transmissions, in order to prevent this lowering, a scan region is limited to a small region including a target such as tumor site or a time region is limited, whereby transmission may be carried out.

The Inventor carried out testing for composition of harmonic components in order to investigate an advantageous effect of the described embodiments and their modified examples. The testing results are shown in FIG. 15 and FIG. 16.

Figure 15:
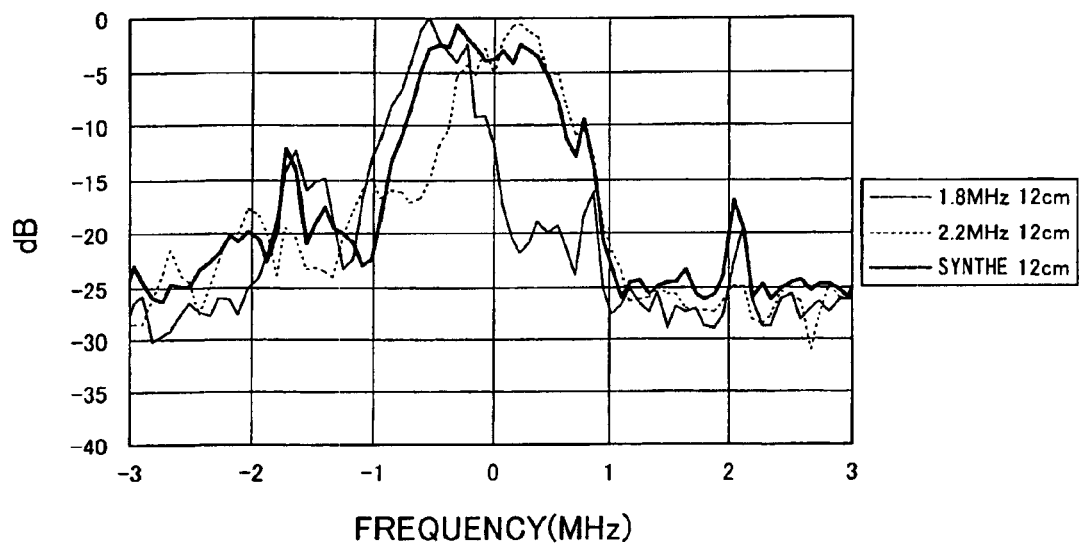
FIG. 15 is a graph depicting the result of a harmonic synthesizing test.

FIG. 15 shows the testing result of harmonic composition when both of the receiving signal obtained by using two types of ultrasonic pulses of 1.8 MHz (number of burst waves: 3) and 2.2 MHz (number of burst waves: 3) are synthesized by THI testing using an agar phantom (in view of interference in time waveforms, although it is ideal to adjust the bandwidths of both harmonic components to be equal to each other, in the present example, the number of burst waves are the same, and the bandwidths are approximately equal to each other because of testing restriction).

According to the testing result shown in FIG. 15, it is verified that a wide-bandwidth THI component can be generated by synthesizing the respective THI component generated by transmissions that are independent of each other.

Figure 16:
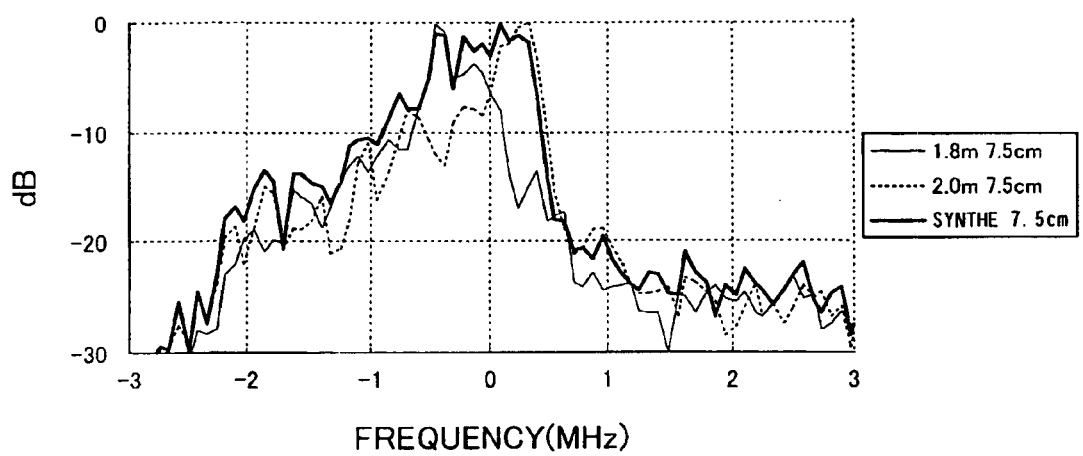
FIG. 16 is a graph depicting the result of another harmonic synthesizing test.

FIG. 16 shows the testing result of harmonic composition when harmonic components of both of the receiving signals obtained by two types of ultrasonic pulses of 1.8 MHz (number of burst waves: 4) and 2.0 MHz (number of burst waves: 4) are synthesized under the condition for a low sound pressure of MI (Mechanical Index)=0.1 by using a contrast medium (bubbles) in the low MI real time perfusion test.

According to the testing result shown in FIG. 16, it is verified that a harmonic component of wide-bandwidth bubbles can be generated by synthesizing a harmonic component of the respective bubbles generated by transmissions that are independent of each other.

The present invention is not limited to the described embodiments and modified examples which are typically shown, and various modifications and alterations can occur to one skilled in the art based on the claims without departing from the spirit of the invention. These modifications and alterations pertain to the claim(s) of the present invention.

What is claimed is:

1. An ultrasonic diagnostic apparatus for scanning a subject to be examined with an ultrasonic pulse, the apparatus comprising:
   transmitting means for transmitting the ultrasonic pulse a plurality of times along each scanning line so as to scan during each time of scanning a region in the subject, transmission characteristics of ultrasonic pulses transmitted along each scanning line during each time of scanning of the region being changed from one another;
   receiving means for receiving an ultrasonic echo signal of each ultrasonic pulse reflected or scattered in the subject and acquiring an electrical reception signal corresponding to each ultrasonic echo signal;
   filter means for applying filtering processing to each reception signal acquired by the receiving means, characteristics of the filtering processing applied to each of the reception signals acquired along each scanning line during each time of scanning of the region being changed from one another and being respectively related in frequency domains to the transmission characteristics of the ultrasonic pulses transmitted along each scanning line during each time of scanning of the region;
   synthesizing means for synthesizing the plurality of reception signals, scanning line by scanning line, filtering-processed by the filter means;
   producing means for producing image data of the region using the reception signals synthesized by the synthesizing means; and
   display means for displaying the image data produced by the producing means.

2. An ultrasonic diagnostic apparatus for scanning a subject to be examined with an ultrasonic pulse, the apparatus comprising:
   a transmitting unit configured to transmit the ultrasonic pulse a plurality of times along each scanning line so as to scan during each time of scanning a region in the subject, transmission characteristics of ultrasonic pulses transmitted along each scanning line during each time of scanning of the region being changed from one another;
   a receiving unit configured to receive an ultrasonic echo signal of each ultrasonic pulse returned from the subject and to acquire an electrical reception signal corresponding to each ultrasonic echo signal;
   a filter configured to apply filtering processing to each reception signal acquired by the receiving unit, characteristics of the filtering processing applied to each of the reception signals acquired along each scanning line during each time of scanning of the region being changed from one another and being respectively related in frequency domains to the transmission characteristics of the ultrasonic pulses transmitted along each scanning line during each time of scanning of the region; and
   a synthesizing unit configured to synthesize the plurality of reception signals, scanning line by scanning line, filtering-processed by the filter.

3. The ultrasonic diagnostic apparatus as claimed in claim 2, wherein the transmitting unit is configured to change a center frequency of the transmission characteristic of each ultrasonic pulse transmitted along each scanning line during each time of scanning of the region.

4. The ultrasonic diagnostic apparatus as claimed in claim 2, wherein the transmitting unit is configured to transmit the ultrasonic pulse of which frequency bandwidth is limited to an extent that a signal component of the reception signal corresponding to a harmonic component of the ultrasonic pulse that has been transmitted is separable from a signal component of the reception signal corresponding to a fundamental component of the ultrasonic pulse that has been transmitted.

5. The ultrasonic diagnostic apparatus as claimed in claim 2, wherein the filter is configured to sample, every time the ultrasonic pulse is transmitted, from the reception signal, a signal component corresponding to a harmonic component of the ultrasonic pulse that has been transmitted and the synthesizing unit is configured to mutually synthesize the harmonic components filtered by the filter in response to transmitting the ultrasonic pulse along each scanning line during each time of scanning of the region.

6. The ultrasonic diagnostic apparatus as claimed in claim 5, wherein the signal component corresponding to the harmonic component, which is synthesized by the synthesizing unit, is broader in a bandwidth than the harmonic component from the filter.

7. The ultrasonic diagnostic apparatus as claimed in claim 5, wherein the harmonic component is a signal component that corresponds to a sub harmonic component of the ultrasonic pulse, the sub harmonic component being generated due to a non linear behavior of an ultrasonic contrast medium administered into the subject.

8. The ultrasonic diagnostic apparatus as claimed in claim 5, wherein the filter is configured to change the characteristic of the filtering processing according to a depth in a direction of each scanning line, the characteristic of the filtering processing being determined so that a predetermined amount of a signal component corresponding to a fundamental component of the ultrasonic pulse is positively left in a signal filtered by the filter.

9. The ultrasonic diagnostic apparatus as claimed in claim 2, wherein the synthesizing unit is configured to mutually add the plurality of reception signals filtering processed by the filter corresponding to each scanning line during each time of scanning of the region.

10. The ultrasonic diagnostic apparatus as claimed in claim 2, further comprising:
a changing unit configured to change, every time the ultrasonic pulse is transmitted a plurality of times along each scanning line during each time of scanning of the region, at least one of parameters including a center frequency and a frequency bandwidth of the ultrasonic pulse, an amplitude of the ultrasonic pulse, an aperture for transmitting the ultrasonic pulse, a focus obtained when the ultrasonic pulse is beam formed, a receiving gain for the reception signal, and an addition coefficient for obtaining the reception signal.

11. The ultrasonic diagnostic apparatus as claimed in claim 2, wherein the transmitting unit is configured to transmit the ultrasonic pulse having a frequency bandwidth in which both a first signal component of the reception signal corresponding to a harmonic component of the ultrasonic pulse and a second signal component of the reception signal corresponding to a fundamental component of the ultrasonic pulse are partially overlapped on each other with regard to spectra of the first and second signal components, and
the filter is configured to extract, from the reception signal, every time of transmitting the ultrasonic pulse along each scanning line during each time of scanning of the region, a signal component having a frequency range falling into a frequency range of the harmonic component, but being outside an overlapped frequency range on the fundamental component.

12. The ultrasonic diagnostic apparatus as claimed in claim 2, wherein the transmitting unit is configured to change both a number of times of transmitting the ultrasonic pulse along each scanning line during each time of scanning of the region and a center frequency of the ultrasonic pulse to be transmitted alone each scanning line during each time of scanning of the region so that physiological attenuation occurring when the ultrasonic pulse and the ultrasonic echo signal propagate through the subject is corrected in the reception signal synthesized by the synthesizing unit.

13. An ultrasonic diagnostic apparatus for scanning a subject to be examined with an ultrasonic pulse, thereby acquiring a harmonic image, said apparatus comprising:
a transmitting unit configured to transmit the ultrasonic pulse a plurality of times along each scanning line so as to scan during each time of scanning a region in the subject, the ultrasonic pulse having a first bandwidth with a spectrum characteristic set to such an extent that a signal component corresponding to a harmonic component of the ultrasonic pulse is separable from a signal component corresponding to a fundamental component of the ultrasound pulse;
a receiving/processing unit configured to receive an echo signal of the ultrasonic pulse responsively to each of the plurality of times of transmission of the ultrasonic pulse along each scanning line during each time of scanning of the region and to process the echo signal received into a harmonic signal having a second bandwidth with a spectrum characteristic broader than the first bandwidth of the transmitted ultrasonic pulse; and
an image producing unit configured to produce a harmonic image from the harmonic signal.

14. An ultrasonic imaging method in which a subject to be examined is scanned by an ultrasonic pulse transmitted and an electrical reception signal that corresponds to an ultrasonic echo signal of the ultrasonic pulse is reflected or scattered in the subject is acquired, said method comprising the steps of:
executing transmission of the ultrasonic pulse, reception of the echo signal, and acquisition of the reception signal, each of the transmission and the reception being carried out a plurality of times along each scanning line to span during each time of scanning the region and transmission characteristics of the ultrasonic pulses transmitted along each scanning line during each time of scanning of the region being changed from one another;
applying filtering processing to each reception signal acquired, characteristics of the filtering processing applied to each of the reception signals acquired along each scanning line during each time of scanning of the region being changed from one another and being respectively related in frequency domains to the transmission characteristics of the ultrasonic pulses transmitted along each scanning line during each time of scanning of the region;
synthesizing the plurality of processed reception signals with each other, scanning line by scanning line;
producing image data of the region scanned by using the synthesized reception signals; and
displaying an image based on the produced image data.

15. The ultrasonic imaging method as claimed in claim 14, wherein the transmitted ultrasonic pulse is changed from each other with respect to a center frequency thereof every time the ultrasonic pulse is transmitted along each scanning line during each time of scanning of the region.

16. The ultrasonic imaging method as claimed in claim 14, wherein the transmitted ultrasonic pulse has a limited frequency bandwidth set to such an extent that a signal component of the reception signal corresponding to a harmonic component of the ultrasonic pulse is separable from a signal component of the reception signal corresponding to a fundamental component of the ultrasonic pulse.

17. The ultrasonic diagnostic apparatus as claimed in claim 16, wherein the harmonic component corresponds to a second harmonic component of the ultrasonic pulse generated due to either a non linearity of physiological tissues of the subject or a non linear behavior of an ultrasonic contrast medium administrated into the subject.

18. The ultrasonic diagnostic apparatus as claimed in claim 14, wherein the filtering processing is set to a process for sampling, every time the ultrasonic pulse is transmitted along each scanning line during each time of scanning of the region, from the reception signal, a signal component that corresponds to a harmonic component of the ultrasonic pulse.

19. The ultrasonic diagnostic apparatus as claimed in claim 18, wherein the signal component corresponding to the harmonic component, which is synthesized at the synthesizing step is broader in a bandwidth than the harmonic component obtained from the filtering processing.

20. The ultrasonic diagnostic method as claimed in claim 14, further comprising the step of changing, every time the ultrasonic pulse is transmitted a plurality of times along each scanning line during each time of scanning of the region, at least one of parameters including a center frequency and a frequency bandwidth of the ultrasonic pulse; an amplitude of the ultrasonic pulse; an aperture for transmitting the ultrasonic pulse; a focus obtained when the ultrasonic pulse is beam formed; a receiving gain for the reception signal; and an addition coefficient for obtaining the reception signal.

21. An ultrasonic diagnostic apparatus for scanning a subject to be examined with an ultrasonic pulse in order to acquire a harmonic image of the subject, said apparatus comprising:

a transmitting unit configured to transmit the ultrasonic pulse a plurality of times along each scanning line so as to scan during each time of scanning a region in the subject, the plurality of times of the ultrasonic pulses to be transmitted including two types of ultrasonic pulses of which signal polarities are opposite to each other, each type of the ultrasonic pulse being transmitted a plurality of times, and transmission characteristics of the ultrasound pulses being changed one from the other;

a receiving unit configured to receive an electrical reception signal that corresponds to an ultrasonic echo signal returned from the subject every time of transmission of the ultrasonic pulse;

a synthesizing unit configured to mutually add, between the two types of transmission, the reception signals to produce a plurality of harmonic components depending on respective transmission characteristics and to mutually synthesize, every time of a transmission, the plurality of harmonic components to broaden a bandwidth of the harmonic component relevant to a fundamental component of the ultrasonic pulse; and an image producing unit configured to produce the harmonic image from the harmonic component of which bandwidth is broadened by the synthesizing unit.

* * * * *